(12) United States Patent
Kume et al.

(10) Patent No.: US 8,257,577 B2
(45) Date of Patent: Sep. 4, 2012

(54) GAS SENSOR AND MANUFACTURING METHOD THEREOF

(75) Inventors: Makoto Kume, Inuyama (JP); Yuichi Yamada, Komaki (JP)

(73) Assignee: NGK Spark Plug Co., Ltd., Aichi (JP)

( * ) Notice: Subject to any disclaimer, the term of this patent is extended or adjusted under 35 U.S.C. 154(b) by 1146 days.

(21) Appl. No.: 12/099,516

(22) Filed: Apr. 8, 2008

(65) Prior Publication Data

US 2008/0277282 A1   Nov. 13, 2008

(30) Foreign Application Priority Data

May 8, 2007 (JP) .................................. 2007-123106
Feb. 8, 2008 (JP) .................................. 2008-029567

(51) Int. Cl.
*G01N 27/26* (2006.01)
*G01N 27/407* (2006.01)

(52) U.S. Cl. ........ 205/781; 204/429; 204/424; 204/410; 204/428; 205/783.5; 205/784.5; 73/23.31; 73/23.32

(58) Field of Classification Search .................. 204/410, 204/411, 421–429; 73/23.31, 23.32; 205/781, 205/783.5–785, 787
See application file for complete search history.

(56) References Cited

U.S. PATENT DOCUMENTS

| | | | |
|---|---|---|---|
| 5,238,551 A | 8/1993 | Katsu et al. | |
| 6,898,961 B2* | 5/2005 | Yamada et al. | 73/31.05 |
| 2004/0035700 A1* | 2/2004 | Taguchi et al. | 204/429 |
| 2006/0237315 A1* | 10/2006 | Matsuo et al. | 204/424 |
| 2007/0160510 A1* | 7/2007 | Schultz et al. | 422/177 |
| 2008/0050205 A1* | 2/2008 | Boltshauser | 413/1 |

FOREIGN PATENT DOCUMENTS

| | | |
|---|---|---|
| EP | 0 581 067 A1 | 2/1994 |
| EP | 0 962 766 A1 | 12/1999 |
| EP | 1 004 876 A1 | 5/2000 |
| EP | 1 707 935 A1 | 10/2006 |
| JP | 4-61056 U | 5/1992 |
| JP | 11160274 A | 6/1999 |

(Continued)

OTHER PUBLICATIONS

Japanese Office Action for corresponding Japanese Application No. 2008-029567.

*Primary Examiner* — Jeffrey T Barton
*Assistant Examiner* — Jennifer Dieterle
(74) *Attorney, Agent, or Firm* — Sughrue Mion, PLLC

(57) ABSTRACT

There is provided a gas sensor, which includes a sensor element extending axially of the gas sensor and having a gas sensing portion at a front end thereof and an electrode portion at a rear end thereof, a cylindrical metal shell retaining therein the sensor element with the gas sensing portion and the electrode portion protruding from front and rear ends of the metal shell, respectively, and having a flange portion and a rear end portion located on a rear side of the flange portion, a cylindrical protection cover having a front end fitted onto the rear end portion of the metal shell so as to cover the electrode portion and a weld joint through which the entire circumference of the front end of the protection cover is joined through the metal shell. The weld joint extends from an end face of the protection cover to the metal shell.

15 Claims, 8 Drawing Sheets

FOREIGN PATENT DOCUMENTS

| | | |
|---|---|---|
| JP | 2001-147213 A | 5/2001 |
| JP | 3092962 U | 1/2003 |
| JP | 2003-161720 A | 6/2003 |
| JP | 2004-354274 A | 12/2004 |
| JP | 2005-072007 A | 3/2005 |
| JP | 2006-153592 A | 6/2006 |
| JP | 2007-101411 A | 4/2007 |
| WO | WO 2005-000498 * | 1/2005 |

* cited by examiner

GAS SENSOR AND MANUFACTURING METHOD THEREOF

BACKGROUND OF THE INVENTION

The present invention relates a gas sensor having a sensor element capable of detecting the concentration of a specific gas component in gas under measurement and a manufacturing method of the gas sensor.

Hereinafter, the term "front" refers to a gas sensing side with respect to the axial direction of a gas sensor, and the term "rear" refers to a side opposite to the front side.

An exhaust gas sensor for an automotive vehicle is known, which includes, a sensor element, a lead wire, a metal shell and a protection cover. The sensor element has a gas sensing portion at a front end thereof to generate a detection signal responsive to the concentration of a specific gas component such as nitrogen oxide (NOx) or oxygen ($O_2$) in exhaust gas and an electrode portion at a rear end thereof connected with the lead wire to output the detection signal from the gas sensing portion to an external device through the lead wire. The metal shell retains therein the sensor element with the gas sensing portion and the electrode portion protruding from front and rear ends of the metal shell, respectively. The protection cover is joined to the metal shell so as to cover and protect the electrical connection between the sensor electrode portion and the lead wire.

In general, the metal shell and the protection cover are joined together by laser welding. Japanese Laid-Open Patent Publication No. 2004-354274 and No. 2001-147213 disclose one such type of weld joint technique in which the metal shell and the protection cover are joined by fitting a front end portion of the protection cover around a rear end portion of the metal shell, optionally swaging the front end portion of the protection cover onto the rear end portion of the metal shell and irradiating a laser beam from the outside of the protection cover to form a laser weld joint between the front end portion of the protection cover and the rear end portion of the metal shell.

SUMMARY OF THE INVENTION

In the above-disclosed welding joint technique, the laser weld joint is formed at a position axially away from a front edge of the protection cover. Through the laser weld joint, an inner circumferential surface of the protection cover and an outer circumferential surface of the metal shell are held very close to each other but may leave a narrow open gap therebetween from the front cover edge to the laser weld joint. There is a case where water penetrates into the narrow gap between the metal shell and the protection cover by capillary action when the gas sensor gets wet during its use. It is unlikely that the water will be volatilized and released from this narrow gap into the outside atmosphere so that the laser weld joint is kept wet for a long time. As a result, the laser weld joint becomes corroded by the water due to the fact that the laser weld joint (notably, the joint interface of the metal shell which has been once molten by laser welding) is relatively susceptible to corrosion by water.

It is therefore an object of the present invention to provide a gas sensor with a corrosion-resistant weld joint structure between a metal shell and a protection cover. It is also an object of the present invention to provide a manufacturing method of the gas sensor.

According to a first aspect of the present invention, there is provided a gas sensor, comprising: a sensor element extending axially of the gas sensor and having a gas sensing portion at a front end thereof and an electrode portion at a rear end thereof; a cylindrical metal shell retaining therein the sensor element with the gas sensing portion and the electrode portion protruding from front and rear ends of the metal shell, respectively, and having a flange portion and a rear end portion located on a rear side of the flange portion; a cylindrical protection cover having a front end fitted onto the rear end portion of the metal shell so as to cover the electrode portion; and a weld joint through which the entire circumference of the front end of the protection cover is joined to the metal shell, wherein the weld joint extends from an end face of the front end of the protection cover to the metal shell.

According to a second aspect of the present invention, there is provided a method of manufacturing a gas sensor, comprising: providing a sensor element, a cylindrical metal shell and a cylindrical protection cover, the sensor element having a gas sensing portion at a front end thereof and an electrode portion at a rear end thereof, the metal shell having a flange portion and a rear end portion located on a rear side of the flange portion and including a first cylindrical section and a second cylindrical section located on a rear side of the first cylindrical section and being smaller in diameter than the first cylindrical section; assembling the sensor element and the metal shell together to retain the sensor element in the metal shell with the gas sensing portion and the electrode portion protruding from front and rear ends of the metal shell, respectively; placing a front end of the protection cover around the second cylindrical section of the rear end portion of the metal shell and allowing an end face of the front end of the protection cover to abut a rear end face of the first cylindrical section of the rear end portion of the metal shell; and laser welding the entire circumference of the front end of the protection cover to the first cylindrical section of the rear end portion of the metal shell to form a weld joint therebetween extending from the end face of the front end of the protection cover to the first cylindrical section of the rear end portion of the metal shell.

According to a third aspect of the present invention, there is provided a method of manufacturing a gas sensor, comprising: providing a sensor element, a cylindrical metal shell and a cylindrical protection cover, the sensor element having a gas sensing portion at a front end thereof and an electrode portion at a rear end thereof, the metal shell having a flange portion and a rear end portion located on a rear side of the flange portion; assembling the sensor element and the metal shell together to retain the sensor element in the metal shell with the gas sensing portion and the electrode portion protruding from front and rear ends of the metal shell, respectively; placing a front end of the protection cover around the rear end portion of the metal shell and allowing an end face of the front end of the protection cover to abut a rear end face of the flange portion of the metal shell; and laser welding the entire circumference of the front end of the protection cover to the flange portion of the metal shell to form a weld joint therebetween extending from the end face of the front end of the protection cover to the flange portion of the metal shell.

According to a fourth aspect of the present invention, there is provided a method of manufacturing a gas sensor, comprising: providing a sensor element, a cylindrical metal shell and a cylindrical protection cover, the sensor element having a gas sensing portion at a front end thereof and an electrode portion at a rear end thereof, the metal shell having a flange portion and a rear end portion located on a rear side of the flange portion; assembling the sensor element and the metal shell together to retain the sensor element in the metal shell with the gas sensing portion and the electrode portion protruding from front and rear ends of the metal shell, respectively; placing a front end of the protection cover around the rear end portion of the metal shell while spacing an end face of the front end of the protection cover away from the flange portion of the metal shell; and laser welding the entire circumference of the front end of the protection cover to the rear end portion of the metal shell to form a weld joint therebetween extending from the end face of the front end of the protection cover to the rear end portion of the metal shell.

The other objects and features of the present invention will also become understood from the following description.

DESCRIPTION OF THE EMBODIMENTS

Figure 1:
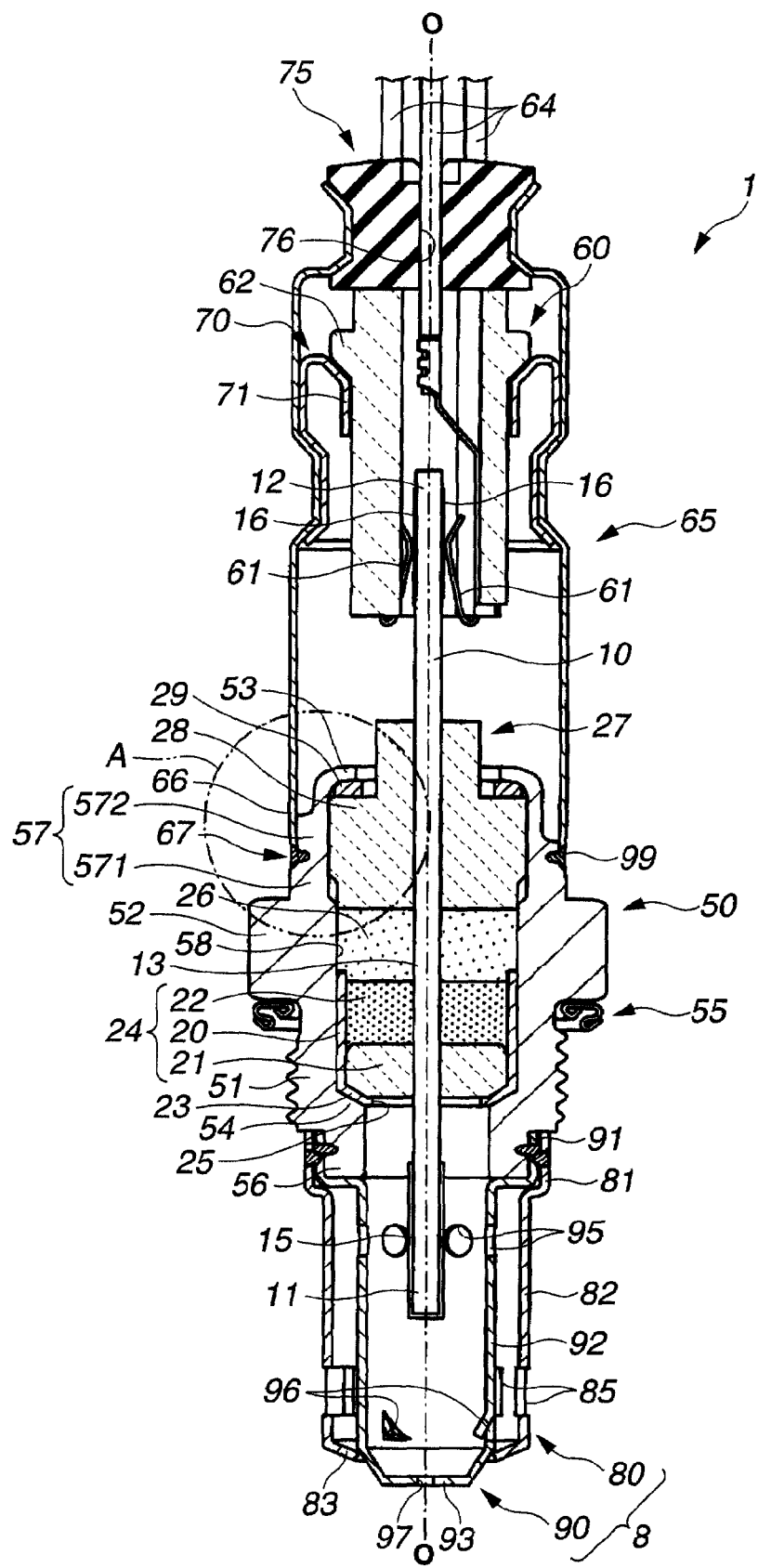
FIG. 1 is a section view of a gas sensor according to a first embodiment of the present invention.

The present invention will be described below by way of the following first to fourth embodiments in which like parts and portions are designated by like reference numerals to omit explanations thereof. Herein, the first to fourth embodiments of the present invention specifically refer to oxygen gas sensors 1, 101, 201 and 301 for automotive vehicles although the present invention can be applied to any other types of gas sensors such as NOx sensors and HC sensors.

First Embodiment

The oxygen gas sensor 1 is mounted on an exhaust pipe of the vehicle to detect the concentration of oxygen ($O_2$) in exhaust gas and generate a detection signal (current signal) responsive to the exhaust oxygen concentration. By way of example, the gas sensor 1 is designed as a so-called universal exhaust gas oxygen sensor for detecting the air/fuel ratio of the exhaust gas based on the exhaust oxygen concentration. When the air/fuel ratio is in a lean range, the detection signal of the universal exhaust gas oxygen sensor corresponds to an excess amount of oxygen with respect to the stoichiometric air/fuel ratio level. When the air/fuel ratio is in a rich range, the detection signal of the universal exhaust gas oxygen sensor corresponds to a required amount of oxygen to allow complete combustion of unburned gas. The detection signal of the gas sensor 1 is transmitted to a sensor control device so that the sensor control device determines the air/fuel ratio of the exhaust gas based on the detection signal of the gas sensor 1 and outputs the exhaust air/fuel ratio to ECU (electronic control unit) for air/fuel ratio feedback control.

Figure 2:
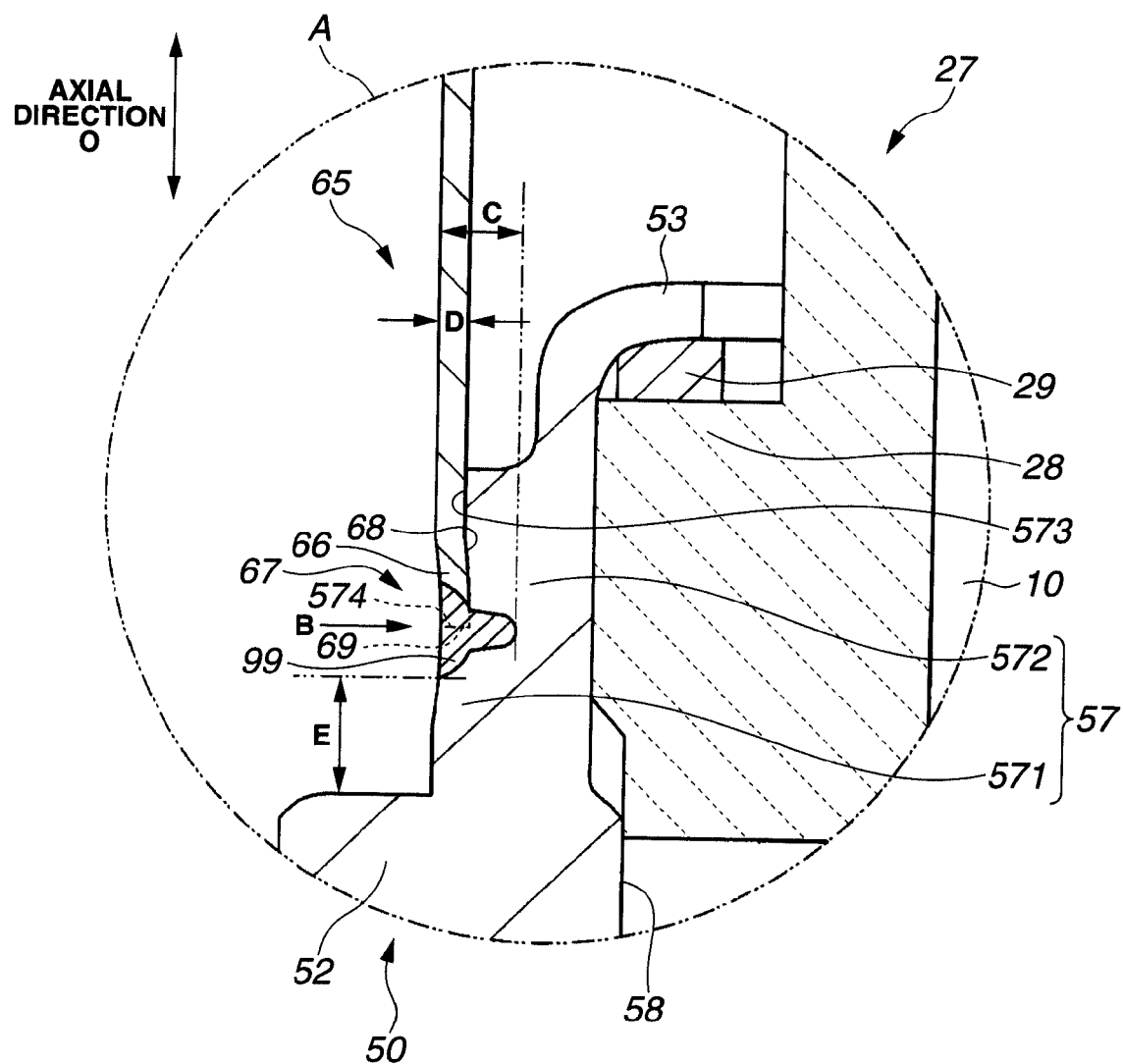
FIG. 2 is an enlarged section view of part A of the gas sensor according to the first embodiment of the present invention.

As shown in FIGS. 1 and 2, the gas sensor 1 includes a sensor element 10, a flange 24, a metal shell 50, a separator 60, a metal fixture 70, front and rear protection covers 8 and 65 and lead wires 64.

The sensor element 10 has an elongated plate shape extending in the direction of an axis O of the gas sensor 1 and includes, at a front end thereof, a gas sensing portion 11 exposed to the exhaust gas inside the exhaust pipe so as to detect the oxygen concentration of the exhaust gas. In order to protect the gas sensing portion 11 from poisoning by the exhaust gas, a protection layer 15 is formed on an outer surface of the gas sensing portion 11.

In the first embodiment, the sensor element 10 consists of a sensor body for detecting the exhaust oxygen concentration and a heater for enabling early activation of the sensor body by heating although not specifically shown in the drawings. The sensor body and the heater are integrally laminated together in a thickness direction of the sensor element 10 (in a horizontal direction in FIG. 1). The sensor body contains a solid electrolyte component predominantly made of zirconia and a sensor electrode predominantly made of platinum and arranged in the gas sensing portion 11. The heater contains a heating component and a heater electrode. The sensor element 10 may alternatively have no heater and thus refer to the sensor body itself.

The sensor element 10 also includes an electrode portion 12 formed at a rear end thereof with five electrode pads 16 to lead out therefrom the sensor and heater electrodes for sensor energization and detection signal output and a middle portion 13 located between the gas sensing portion 11 and the electrode portion 12. (It is noted that only two of the five electrode pads 16 are shown in FIG. 1 for simplicity.)

The flange 24 is integrally attached around a front side of the middle portion 13 of the sensor element 10 so that the sensor element 10 is retained by the flange 24 in the metal shell 50.

In the first embodiment, the flange 24 includes a metal cup 20, a ceramic ring 21 of alumina and a seal material 20 of talc powder. The metal cup 20 has a bottomed cylindrical shape with a tapered outer bottom edge 23 and a bottom hole 25 so that the sensor element 10 is inserted in the metal cup 20 with the gas sensing portion 11 protruding through the bottom hole 25. The ceramic ring 21 placed on the bottom of the metal cup 20 and around the sensor element 10. The seal material 22 is compacted into the metal cup 20 so that the metal cup 20, the ceramic ring 21 and the seal material 22 are integrated into one piece.

The metal shell 50 is made of low-carbon steel such as SUS430 and fixed to the exhaust pipe to mount the gas sensor 1 on the exhaust pipe. The metal shell 50 has a cylindrical shape with an axial through hole 58 to retain therein the middle portion 13 of the sensor element 10 together with the flange 24 with the gas sensing portion 11 and the electrode portion 12 of the sensor element 10 protruding from front and rear ends of the metal shell 50, respectively. A rear-facing step 54 is formed on an inner circumferential wall of the through hole 58 to support thereon the front outer edge 23 of the metal cup 20.

The metal shell 50 includes an external thread portion 51, a tool engagement portion 52 and front and rear cover engagement portions 56 and 57 on an outer circumferential surface thereof. The external thread portion 51 is formed in a front side of the outer circumferential surface of the metal shell 50 at around a location corresponding to the inner step 54 so as to be screwed into the exhaust pipe. The tool engagement portion 52 (as a flange portion) protrudes radially outwardly through the middle of the outer circumferential surface of the metal shell 50 so as to engage with a sensor mounting tool. The front cover engagement portion 56 is formed on a front side of the external thread portion 52 so as to engage with the front protection cover 8, whereas the rear cover engagement portion 57 (as a rear end portion) is formed on a rear side of the tool engagement portion 52 so as to engage with the rear protection cover 65.

In the first embodiment, the rear cover engagement portion 57 contains a cylindrical section 571 and a small-diameter cylindrical section 572 having a smaller diameter than the cylindrical section 571 to define a rear-facing step 574 between these two cylindrical sections 571 and 572 (i.e. a rear end face of the cylindrical section 571) as shown by a dotted line in FIG. 2. The radial dimension of the step 574 is substantially the same as the thickness of the protection cover 65.

A gasket 55 is fitted around the metal shell 50 at a location between a rear end of the external thread portion 51 and a front end of the tool engagement portion 52. When the gas sensor 1 is mounted on the gas sensor 1, the gasket 55 is held between the exhaust pipe and the tool engagement portion 52 and provides a seal against gas leakage from between the gas sensor 1 and the exhaust pipe. Further, a seal material 26 of talc powder is placed in the metal shell 50 and around the sensor element 10 on a rear side of the flange 24. A cylindrical sleeve 27 is also placed in the metal shell 5 and around the sensor element 10 and holds down the seal material 26 from the rear.

The metal shell 50 further includes a swaged portion 53 formed by swaging the metal shell 50 at a rear side of the cover engagement portion 57 onto a stepped rear shoulder end portion 28 of the sleeve 27 so as to retain the sensor element 10 in the metal shell 50. An annular packing 29 is disposed between the swaged portion 53 of the metal shell 50 and the shoulder end portion 28 of the sleeve 27 and provides a seal against combustion gas leakage from through the swaged portion 53 of the metal shell 50.

The separator 60 is formed of insulating ceramic in a cylindrical shape and capped around the electrode portion 12 of the sensor element 10. Five connection terminals 61 are held on an inner circumferential surface of the separator 60 and electrically contacted (connected) at one ends thereof to the electrode pads 16 and at the other ends thereof to the to the lead wires 64, respectively, such that the separator 50 accommodates therein and protects the electrical contacts between the terminals 61 and the electrode pads 16 and between the terminals 61 and the lead wires 64. (It is that two of the fine connection terminals 61 and three of the five lead wires 64 are shown in FIG. 1 for simplicity.)

The rear protection cover 65 is made of stainless steel such as SUS304 and joined at a front end 66 thereof to the metal shell 50 so as to cover and protect therein the electrode portion 12 of the sensor element 10 and the separator 60.

More specifically, the entire circumference of the front end 66 of the protection cover 65 is fitted and joined through a weld joint 99 onto the cover engagement portion 57 of the metal shell 50, with an inner circumferential surface 68 of the front end 66 of the protection cover 65 facing an outer circumferential surface 573 of the small-diameter section 572 of the cover engagement portion 57 and an end face 69 of the front end 66 of the protection cover 65 abutting the step 574 of the cover engagement portion 57. (The axial position at which the front end face 69 of the protection cover 65 abuts the step 574 of the cover engagement portion 57 i.e. the axial interface between the front end face 69 of the protection cover 65 and the step 574 of the cover engagement portion 57 as indicated by an arrow B in FIG. 2 is hereinafter referred to as a cover-to-shell abutting position or interface.)

The weld joint 99 is formed by laser welding so as to extend from the front end face 69 of the protection cover 65 to the cover engagement portion 57 (notably, the cylindrical section 571) of the metal shell 50. Even if there is a narrow gap left between the inner circumferential surface 68 of the front end 66 of the protection cover 65 and the outer circumferential surface 573 of the cover engagement portion 57 of the metal shell 50, this narrow circumferential gap is hermetically sealed and cut off from the outside by the weld joint 99. When the gas sensor 1 gets wet during its use, the weld joint 99 prevents water from penetrating and accumulating into the circumferential gap between the metal shell 50 and the protection cover 65 so that the water does not come into contact with the weld joint 99 for a long time. As shown in FIG. 2, the weld joint 99 is exposed to the outside at around the outer circumferential surface of the cylindrical section 571 of the cover engagement portion 57. The water may adhere to such an exposed open circumferential area of the weld joint 99. However, the exposed circumferential area of the weld joint 99 is relatively large as compared to that of the conventional weld joint. The water can be thus readily volatized from the exposed circumferential area of the weld joint 99 to the outside atmosphere. It is accordingly possible in the first embodiment to protect the weld joint 99 from corrosion caused by long-time contact of the weld joint 99 with the water. It is further possible to allow easy positioning and tentative fixing of the protection cover 65 onto the metal shell 50, at the occasion of laser welding, by engagement of the inner circumferential surface 68 of the protection cover 65 with the outer circumferential surface 573 of the metal shell 50 and by engagement of the front end face 69 of the protection cover 65 with the step 574 of the metal shell 50.

The laser welding is performed by irradiating a laser beam such as a known LAG layer beam onto the cover-to-shell abutting position and its vicinity fully circumferentially from the outside of the protection cover 65. The laser-irradiated areas of the front end 66 of the protection cover 65 and the cover engagement portion 57 of the metal shell 50 are molten so that the molten constituents are mixed to form the weld joint 99. As long as the weld joint 88 extends from the front end face 69 of the protection cover 65 to the cover engagement portion 57 of the metal shell 50 and seals the gap between the metal shell 50 and the protection cover 65, the irradiation position of the laser beam may lean to the side of the metal shell 50 or the protection cover 65 with respect to the cover-to-shell abutting position. When the laser beam is irradiated onto the cover-to-shell abutting position and its vicinity in a direction perpendicular to the direction of the sensor axis O, however, the front end 66 of the protection cover 65 and the cover engagement portion 57 of the metal shell 50 can be molten equally to form the weld joint 99 for assured sealing of the gap between the metal shell 50 and the protection cover 65.

In the first embodiment, the weld joint 99 preferably has a penetration depth C (i.e. a dimension in a radial direction of the gas sensor 1) larger than at least the thickness D of the protection cover 65 as shown in FIG. 2. More preferably, the penetration depth C of the weld joint 99 is two or more times larger than the thickness D of the protection cover 65. The penetration depth C of the weld joint 99 can be controlled by adjusting the laser output during the welding. By such welding control, the front end 66 of the protection cover 65 and the cover engagement portion 57 of the metal shell 50 can be molten and mixed properly to form the weld joint 99 with increased strength for more assured sealing of the gap between the metal shell 50 and the protection cover 65.

Further, the front end of the weld joint 99 is located at a distance E of 1 mm or larger (e.g. 3 mm) axially away from the rear end of the tool engagement portion 52 of the metal shell 50 in the first embodiment. By such location control, the laser beam can be easily irradiated onto the cover-to-shell abutting position. If the distance E between the weld joint 99 and the tool engagement portion 52 is less than 1 mm, the irradiation position of the laser beam is too close to the tool engagement portion 52. It is thus difficult to irradiate the laser beam onto the cover-to-shell abutting position from the direction perpendicular to the direction of the sensor axis O without the laser beam falling on the tool engagement portion 52. If the laser beam falls on the tool engagement portion 52, it becomes difficult to melt the metal shell 50 and the protection cover 65 equally under the laser irradiation. Moreover, the weld joint 99 may result in an ugly finish. In this case, there arises a need to adjust the laser irradiation angle and/or increase the laser irradiation accuracy.

Prior to the laser welding, the entire circumference of the front end 66 of the protection cover 65 and the cover engagement portion 57 of the metal shell 50 are swaged radially inwardly to form a ring-shaped swaged part 67 astride the cover-to-shell abutting position from the front end face 69 of the protection cover 65 to the cylindrical section 571 of the cover engagement portion 57 of the metal shell 50 as shown in FIG. 2. By the formation of such a swaged part 67, the front end 66 of the protection cover 65 is positioned and tentatively fixed onto the cover engagement portion 57 of the metal shell 50 so as to prevent a displacement of the protection cover 65 relative to the metal shell 50 during the welding. The weld joint 99 can be thus formed easily and assuredly by the irradiation of the laser beam.

The metal fixture 70 is arranged between the separator 60 and the protection cover 65 to support the separator 60 by engagement of a flange portion 62 of the separator 60 on an inwardly-bent rear end portion 71 of the metal fixture 70. By swaging the protection cover 65 onto the metal fixture 70, the separator 70 and the separator 60 are held together in the protection cover 65.

A fluorinated-rubber grommet 75 is fixed in the rear end of the protection cover 65 by swaging the rear end of the protection cover 65 onto the grommet 75 while pushing the grommet 75 toward the front. Further, five wire insertion holes 65 are formed in the grommet 75 so that the lead wires 64 are passed hermetically through the wire insertion holes 65, respectively, and led to the outside of the gas sensor 1.

The front protection cover 8 is joined at a rear end thereof to the cover engagement portion 56 of the metal shell 50 so as to cover and protect therein the gas sensing portion 11 of the sensor element 10 from fouling by any exhaust gas deposit (e.g. fuel ash or oil component) and thermal shock and breaking by water.

In the first embodiment, the protection cover 8 has a double structure consisting of an outer cover member 80 and an inner cover member 90 placed in the outer cover member 80 with a gap left between an outer circumferential surface of the inner cover member 90 and an inner circumferential surface of the outer cover member 80 as shown in FIG. 1.

The inner cover member 90 has a bottomed cylindrical shape with a circumferential wall 92 and a front bottom wall 93. A plurality of gas introduction holes 95 are formed in a rear side of the circumferential wall 92, whereas a plurality of drain holes 96 are in a front side of the circumferential wall 92. A discharge hole 97 is formed in the bottom wall 93. The inner cover member 90 is fixed to the metal shell 50 by engaging a rear open end 91 of the inner cover member 90 around the cover engagement portion 56 of the metal shell 50 and then laser welding the rear end 91 of the inner cover member 90 circumferentially to the cover engagement portion 56 of the metal shell 50.

The outer cover member 80 has a cylindrical shape with a circumferential wall 82. A plurality of gas introduction holes 85 are formed in a front side of the circumferential wall 82. The outer cover member 80 is fixed the metal shell 50 via the inner cover member 90 by engaging a rear end 81 of the outer cover member 80 around the rear end 91 of the inner cover member 90 and spot welding the rear end 81 of the outer cover member 80 circumferentially to the rear end 91 of the inner cover member 90. A front end 83 of the outer cover member 80 is inwardly bent toward and brought into contact with the circumferential wall 92 of the inner cover member 90 so as to close the gap between the outer cover member 80 and the inner cover member 90.

When the exhaust gas is introduced into the outer cover member 80 through the outer gas introduction holes 85, there occurs a swirl of the exhaust gas within the gap between the cover members 80 and 90. By this swirl, water (moisture) and any deposit component is separated from the exhaust gas. After that, the exhaust gas is introduced into the inner cover member 90 through the inner gas introduction holes 95, flows to the gas sensing portion 11 of the sensor element 10, and then, is discharged to the outside through the discharge hole 97. The separated water and deposit component is fed into the inner protection cover 90 through the drain holes 96 and discharged to the outside through the discharge hole 97. In this way, the double-structure protection cover 8 performs the function of protecting the gas sensing portion 11 of the sensor element 10 from fouling by the deposit of the exhaust gas and thermal shock and breaking by the water.

Alternatively, the front protection cover 8 may be joined to the cover engagement portion 56 of the metal shell 50 in the same manner as the rear protection cover 65. When the gas sensor 1 is mounted on the exhaust pipe, the front protection cover 8 is located inside of the exhaust pipe. In contrast to the rear protection cover 65 located outside of the exhaust pipe, the front protection cover 8 is exposed to the high-temperature exhaust gas (of e.g. 800° C.) inside the exhaust pipe during the use of the gas sensor 1. Water is easily volatized under such a high-temperature condition if it gets in a gap between the metal shell 50 and the front protection cover 8. It is thus possible to prevent corrosion of the weld joint between the metal shell 50 and the front protection cover 8 more effectively by spreading the weld joint over the metal shell 50 and the front protection cover 8.

The above gas sensor 1 can be manufactured as follows. It is herein noted that the following explanations will concentrate on the joining of the metal shell 50 and the protection cover 65. The manufacturing processes of the other sensor components are known and thus will not explained or will be explained briefly.

In metal shell forming process, the metal shell 50 is formed by subjecting a low-carbon steel pipe to forging (e.g. extrusion) with a cold forging machine, shaping inner and outer circumferential surfaces of the steel pipe with a cutting machine to form the tool engagement portion 52, the cover engagement portions 56 and 57, the through hole 58 and the like, and then, processing the steel pipe with a component rolling die to form the external thread portion 51.

On the other hand, the sensor element 10 is formed by sintering a laminate of green sensor body (solid electrolyte component, electrode and insulator) and green heater body. The protection film 15 is then applied to the gas sensing portion 11 of the sensor element 10.

In assembling process, the metal cup 20, the ceramic ring 21 and the seal material 22 are fitted from the rear to the front side of the middle portion 13 of the sensing element 10. When the seal material 22 is pressed against the ceramic ring 21 and compacted in the metal cup 20 in this state, the metal cup 20, the ceramic ring 21 and the seal material 22 are integrated into the flange 24. Further, the front protection cover 8 is joined to the cover engagement portion 56 of the metal shell 50. The subassembly of the sensing element 10 and the flange 24 is placed in the axial through hole 68 of the metal shell 50. The seal material 26, the sleeve 27 and the packing 29 are further fitted onto the sensor element 10 from the rear. The metal shell 50 is swaged onto the sleeve 27 to compact the seal material 26 in the gap between the metal shell 50 and the sensor element 10 and thereby retain the sensor element 10 in the metal shell 50. Separately, the rear protection cover 65 is formed of stainless steel in a cylindrical shape. The separator 60 with the connection terminals 61 connected to the lead wires 64, the metal fixture 70 and the grommet 75 are fixed together in the protection cover 65 by swaging the rear end of the protection cover 65 radially inwardly.

In cover placement process, the front end 66 of the protection cover 65 is fitted and placed around the small-diameter section 572 of the cover engagement portion 57 of the metal shell 50. At this time, the front end face 69 of the protection cover 65 abuts the step 574 of the cover engagement portion 57 and the inner circumferential surface 68 of the front end 66 of the protection cover 65 faces the outer circumferential surface 573 of the small-diameter section 572 of the cover engagement portion 57 as explained above.

Figure 3:
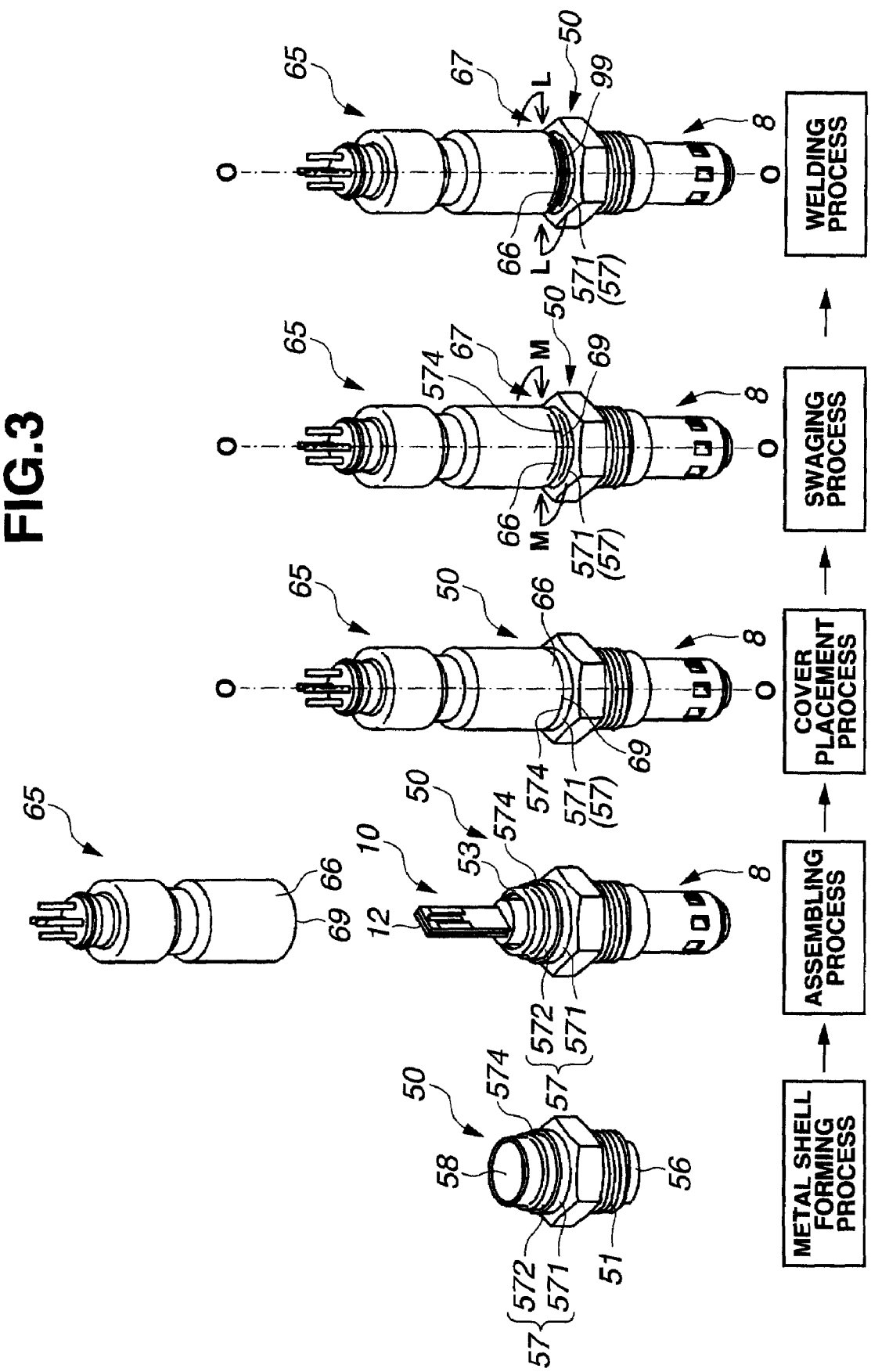
FIG. 3 is a schematic view of how to manufacture the gas sensor according to the first embodiment of the present invention.

In swaging process, the front end 66 of the protection cover 65 and the cylindrical section 571 of the cover engagement portion 57 of the metal shell 50 are swaged radially inwardly as indicated by an arrow M in FIG. 3 to form the swaged part 67 circumferentially at around the cover-to-shell abutting interface for tentative fixing of the protection cover 65 to the metal shell 50.

In welding process, the laser beam is irradiated to the cover-to-shell abutting interface and its vicinity in the direction perpendicular to the direction of the sensor axis O as indicated by an arrow L. Under the laser irradiation, the weld joint 99 is formed circumferentially astride from the front end face 69 of the protection cover 65 to the cylindrical section 571 of the metal shell 50. The gas sensor 1 is completed upon formation of the weld joint 99.

As explained above, the gas sensor 1 can be easily and efficiently produced with the corrosion-resistant weld joint 99 between the metal shell 50 and the protection cover 65.

Second Embodiment

Figure 4:
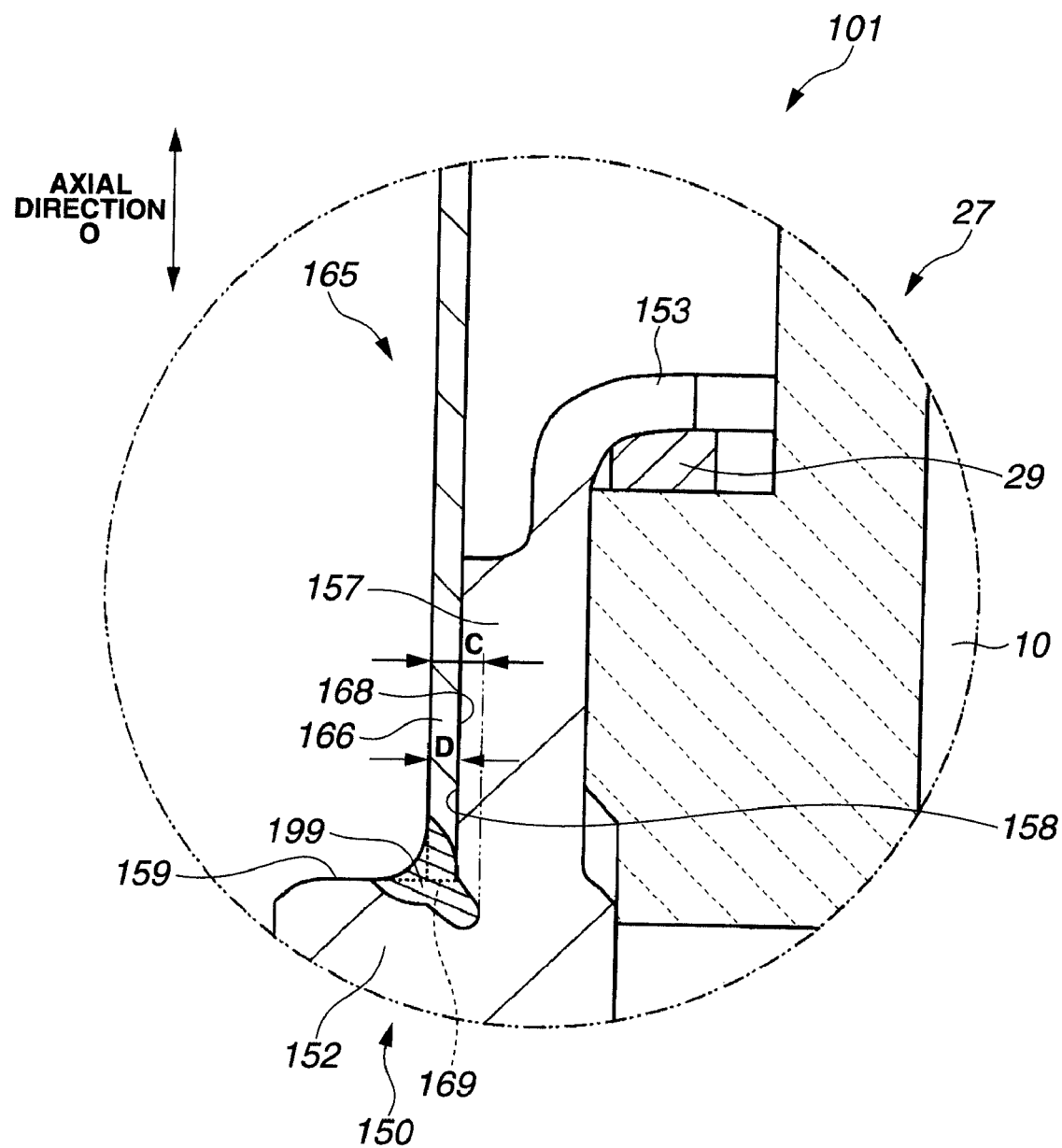
FIG. 4 is an enlarged section view of part of a gas sensor according to a second embodiment of the present invention.
Figure 5:
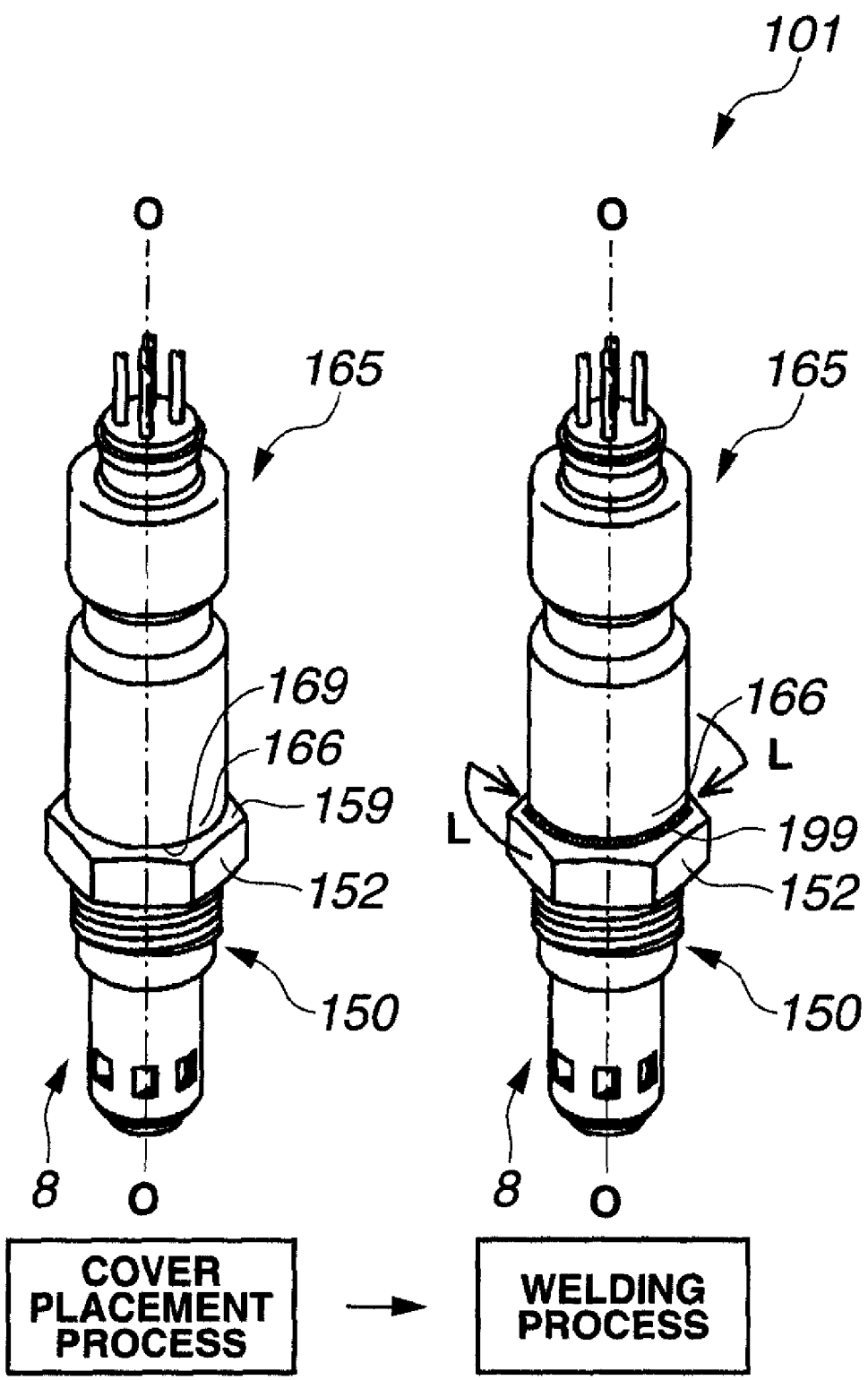
FIG. 5 is a schematic view of how to manufacture the gas sensor according to the second embodiment of the present invention.

The gas sensor 101 of the second embodiment is structurally similar to the gas sensor 1 of the first embodiment, except that the gas sensor 101 has a metal shell 150 and a rear protection cover 165 joined together by a different joint structure as shown in FIGS. 4 and 5.

The metal shell 150 has a tool engagement portion 152 (as a flange portion) and a rear cover engagement portion 157 (as a rear end portion) on a rear side of the tool engagement portion 152. As shown in FIG. 4, no step is formed on the cover engagement portion 157 of the metal shell 150.

The protection cover 165 has a front end 166 joined through a weld joint 199 to the metal shell 150 so as to cover and protect therein the electrode portion 12 of the sensor element 10. The front end 166 of the protection cover 165 has such an inner diameter and length that an inner circumferential surface 168 of the front end 166 mates with an outer circumferential surface 158 of the cover engagement portion 157 of the metal shell 150 and an end face 169 of the front end 166 of the protection cover 165 abuts a rear end face 159 of the tool engagement portion 152 of the metal shell 150 as shown by a dotted line in FIG. 4 in the second embodiment.

For manufacturing of the gas sensor 101, the metal shell 150 is formed in the metal shell forming process and assembled with the protection cover 8 and the sensing element 10 etc. in the assembling process as in the case of the first embodiment. Further, the protection cover 165 is assembled with the separator 60 and the grommet 75 etc.

In the cover placement process, the front end of 166 of the protection cover 165 is fitted and placed around the cover engagement portion 157 of the metal shell 150 by engagement of the inner circumferential surface 168 of the front end 166 of the protection cover 165 with the outer circumferential surface 158 of the cover engagement portion 157 of the metal shell 150 and by engagement of the front end face 169 of the protection cover 165 with the rear end face 159 of the tool engagement portion 152 of the metal shell 150 as shown in FIG. 5.

In the subsequent welding process, the weld joint 199 is formed by laser welding completely circumferentially as indicated by an arrow L in FIG. 5 from the front end face 169 of the protection cover 165 to the tool engagement portion 152 of the metal shell 150 so as to seal out water from the gap between the metal shell 150 and the protection cover 165.

It is therefore possible in the second embodiment to protect the weld joint 199 from corrosion caused by long-time contact of the weld joint 199 with water as in the case of the first embodiment.

In the second embodiment, the laser beam is preferably irradiated onto the cover-to-shell abutting position (interface) and its vicinity from the rear side with respect to the direction perpendicular to the direction of the sensor axis O. The laser-irradiated areas of the front end 166 (including the front end face 169) of the protection cover 165 and the tool engagement portion 152 of the metal shell 150 can be molten equally to form the weld joint 199 for assured sealing of the gap between the outer circumferential surface 158 of the metal shell 150 and the inner circumferential surface 168 of the protection cover 165. Under this laser irradiation, the resulting weld joint 199 extends toward the front as close to the sensor axis O and reaches deeply inside the metal shell 150 as shown in FIG. 4 for increased joint strength.

Further, the exposed outer circumferential area of the weld joint 199 is preferably curved in concave form such as meniscus form as shown in FIG. 4, so that the weld joint 199 can attain a sufficient thickness to close an opening of the gap between the metal shell 150 and the protection cover 165 for assured sealing of the gap between the metal shell 150 and the protection cover 165.

For further joint strength improvement, the penetration depth C of the weld joint 199 is made larger than at least the thickness D of the protection cover 165 by adjusting the laser output during the welding as in the case of the first embodiment.

Third Embodiment

Figure 6:
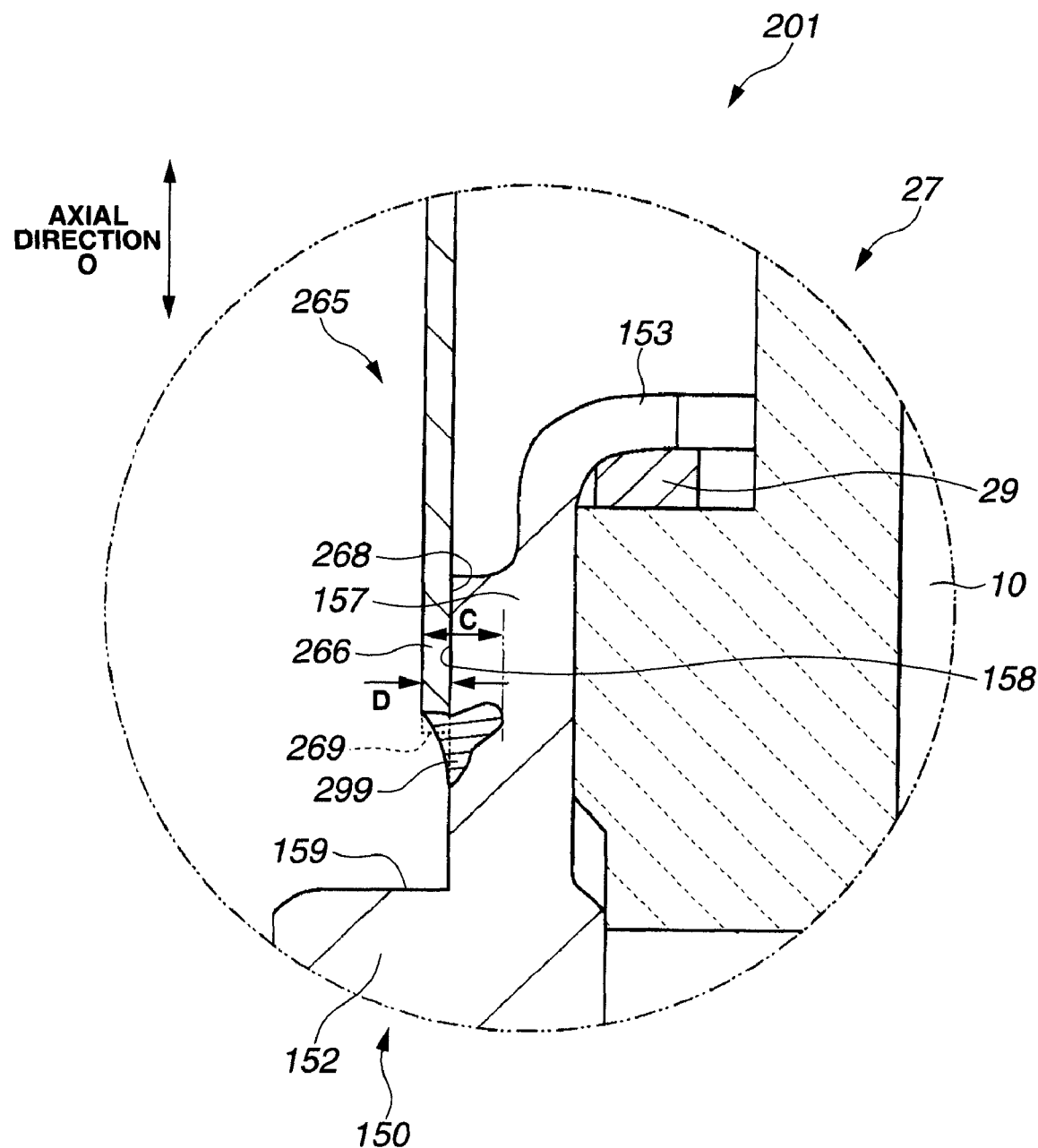
FIG. 6 is an enlarged section view of part of a gas sensor according to a third embodiment of the present invention.
Figure 7:
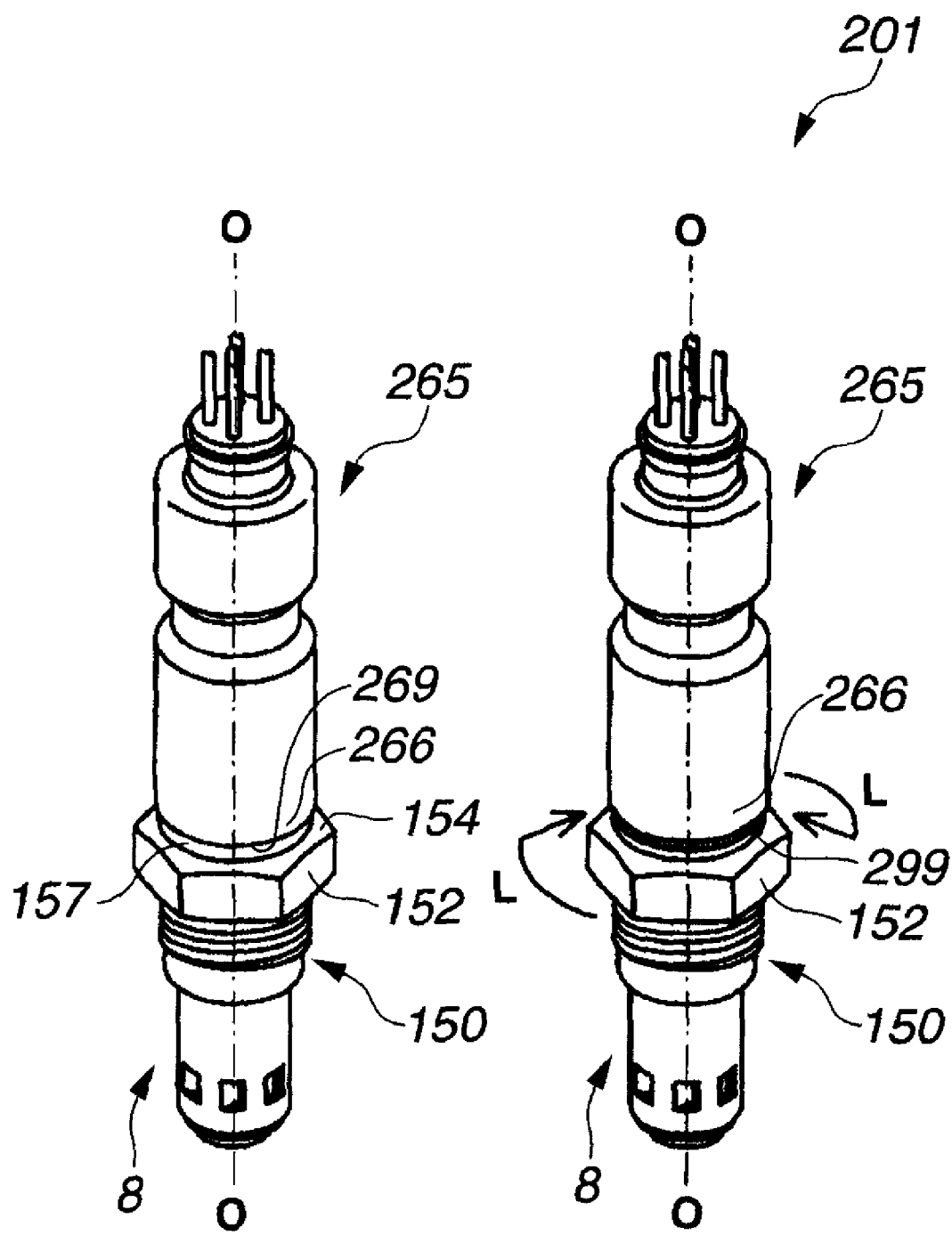
FIG. 7 is a schematic view of how to manufacture the gas sensor according to the third embodiment of the present invention.

The gas sensor 201 of the third embodiment is structurally similar to the gas sensor 101 of the second embodiment, except that the gas sensor 201 has a metal shell 150 and a rear protection cover 265 joined together by a different joint structure as shown in FIGS. 6 and 7.

The metal shell 150 is common to the second and third embodiments. Namely, the metal shell 150 has a tool engagement portion 152 (as a flange portion) and a rear cover engagement portion 157 (as a rear end portion) formed with no step on a rear side of the tool engagement portion 152.

The protection cover 265 has a front end 266 joined through a weld joint 299 to the metal shell 150 so as to cover and protect therein the electrode portion 12 of the sensor element 10. As shown in FIG. 6, the protection cover 265 is substantially equal in inner diameter to the protection cover 165 but is shorter in length than the protection cover 165 to keep a front end face 269 of the protection cover 265 spaced away from the tool engagement portion 152 of the metal shell 150.

For manufacturing of the gas sensor 201, the metal shell 150 is formed in the metal shell forming process and assembled with the protection cover 8 and the sensing element 10 etc. in the assembling process as in the case of the first and second embodiments. Further, the protection cover 265 is assembled with the separator 60 and the grommet 75 etc.

In the cover placement process, the front end 266 of the protection cover 265 is placed around the cover engagement portion 157 of the metal shell 150 by engagement of an inner circumferential surface 268 of the front end 266 of the protection cover 265 with an outer circumferential surface 158 of the cover engagement portion 157 of the metal shell 150. At this time, the front end face 269 of the front end 266 of the protection cover 265 is spaced away from a rear end face 159 of the tool engagement portion 152 of the metal shell 150 because of the shorter length of the protection cover 265 as explained above.

In the subsequent welding process, the weld joint 299 is formed by laser welding completely circumferentially as indicated by an arrow L in FIG. 7 from the front end face 269 of the protection cover 265 to the cover engagement portion 157 of the metal shell 150 so as to seal out water from the gap between the metal shell 150 and the protection cover 265.

It is therefore possible in the third embodiment to protect the weld joint 299 from corrosion caused by long-time contact of the weld joint 299 with water as in the case of the first and second embodiments.

In the third embodiment, the laser beam is preferably irradiated onto the cover-to-shell abutting position (interface) and its vicinity from the front side with respect to the direction perpendicular to the direction of the sensor axis O. The laser-irradiated areas of the front end 266 (including the front end face 269) of the protection cover 265 and the cover engagement portion 157 of the metal shell 150 can be molten equally to form the weld joint 299 for assured sealing of the gap between the outer circumferential surface 158 of the metal shell 150 and the inner circumferential surface 268 of the protection cover 265. Under this laser irradiation, the resulting weld joint 299 extends toward the rear as close to the sensor axis O and reaches deeply inside the metal shell 150 as shown in FIG. 6 for increased joint strength.

Further, the exposed outer circumferential area of the weld joint 299 is preferably curved in concave form such as meniscus form as shown in FIG. 6, so that the weld joint 299 can attain a sufficient thickness to close an opening of the gap between the metal shell 150 and the protection cover 265 for assured sealing of the gap between the metal shell 150 and the protection cover 265.

For further joint strength improvement, the penetration depth C of the weld joint 299 is made larger than at least the thickness D of the protection cover 265 by adjusting the laser output during the welding as in the case of the first and second embodiments.

Fourth Embodiment

Figure 8:
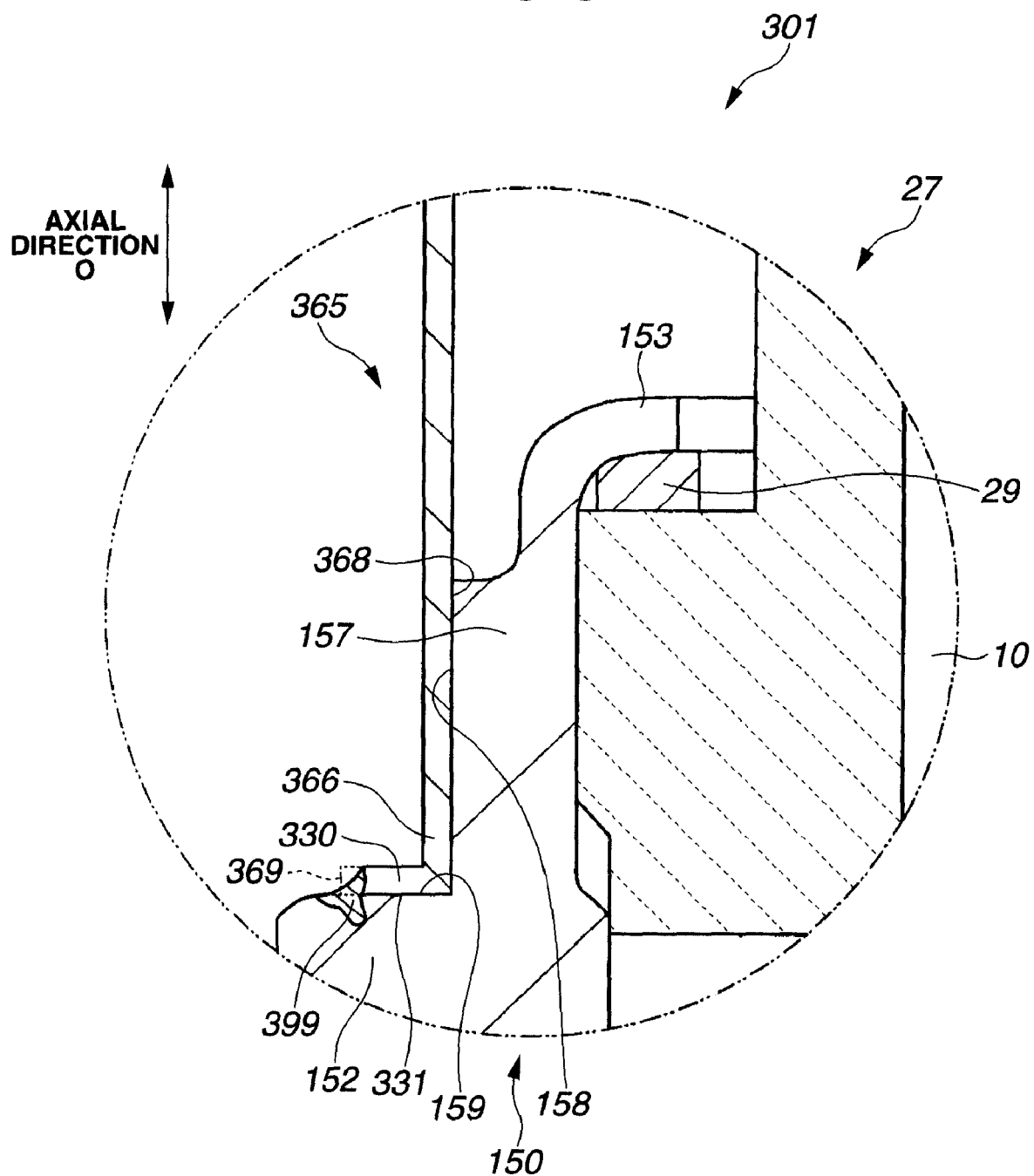
FIG. 8 is an enlarged section view of part of a gas sensor according to a fourth embodiment of the present invention.

The gas sensor 301 of the fourth embodiment is structurally similar to the gas sensor 101 of the second embodiment, except that the gas sensor 301 has a metal shell 150 and a rear protection cover 365 joined together by a different joint structure as shown in FIG. 8.

The metal shell 150 is also common to the second, third and fourth embodiments. Namely, the metal shell 150 has a tool engagement portion 152 (as a flange portion) and a rear cover engagement portion 157 (as a rear end portion) formed with no step.

The protection cover 365 has a front end 366 joined through a weld joint 399 to the metal shell 150 so as to cover and protect therein the electrode portion 12 of the sensor element 10. Although the inner diameter and length of the protection cover 365 are substantially equal to those of the protection cover 165, a radially outwardly protruding large-diameter portion 330 is formed at a front edge on the front end 66 of the protection cover 365 as shown in FIG. 8. The front end 366 of the protection cover 365 is thus placed around the cover engagement portion 157 of the metal shell 150 by engagement of an inner circumferential surface 368 of the front end 366 of the protection cover 365 with an outer circumferential surface 158 of the cover engagement portion 157 of the metal shell 150 and by engagement of a front end face 331 of the large-diameter portion 330 of the protection cover 665 with a rear end face 159 of the tool engagement portion 152 of the metal shell 150. At this time, a radially outward end face 369 of the large-diameter portion 330 of the protection cover 365 is positioned on the rear end face 159 of the tool engagement portion 152 of the metal shell 150 so that the abutting interface between the front end face 369 of the protection cover 365 and the rear end face 159 of the tool engagement portion 152 of the metal shell 150 is open wide to the rear. By irradiating the laser beam onto this cover-to-shell abutting interface, the weld joint 399 is formed completely circumferentially from the front end face 369 of the protection cover 365 to the tool engagement portion 152 of the metal shell 150 so as to seal out water from the gap between the outer circumferential surface 158 of the metal shell 150 and the inner circumferential surface 368 of the protection cover 365.

It is therefore possible in the fourth embodiment to protect the weld joint 399 from corrosion caused by long-time contact of the weld joint 399 with water as in the case of the first to third embodiments.

In the fourth embodiment, the laser beam can be irradiated onto the cover-to-shell abutting position (interface) in the direction of the sensor axis O as long as the front end 366 (including the front end face 369) of the protection cover 365 and the tool engagement portion 152 of the metal shell 150 can be molten properly to form the welding joint 399 from the front end face 369 of the protection cover 365 to the tool engagement portion 152 of the metal shell 150. However, the laser beam is preferably irradiated onto the cover-to-shell abutting position (interface) and its vicinity such that the resulting weld joint 399 extends toward the front as close to the sensor axis O and reaches deeply inside the metal shell 150 as shown in FIG. 8 for increased joint strength as in the case of the second embodiment. Further, the exposed outer circumferential area of the weld joint 399 is preferably curved in concave form such as meniscus form as shown in FIG. 8 as in the case of the first to third embodiments, so that the weld joint 399 can attain a sufficient thickness to close an opening of the gap between the metal shell 150 and the protection cover 365 for assured sealing of the gap between the metal shell 150 and the protection cover 365. For further joint strength improvement, the penetration depth of the weld joint 399 is made larger than at least the thickness of the protection cover 365 by adjusting the laser output during the welding as in the case of the first to third embodiments.

Prior to the laser welding, the front end face 331 of the large-diameter portion 330 of the protection cover 365 and the rear end face 159 of the tool engagement portion 152 of the metal shell 150 may joined together by resistance welding. This makes it possible to seal the gap between the front end face 331 of the large-diameter portion 330 of the protection cover 365 and the rear end face 159 of the tool engagement portion 152 of the metal shell 150 and thereby completely seal out water from the gap between the outer circumferential surface 158 of the metal shell 150 and the inner circumferential surface 368 of the protection cover 365. This also makes it possible to allow positioning (tentative fixing) of the front end face 369 of the large-diameter portion 330 of the protection cover 365 onto the rear end face 159 of the tool engagement portion 152 of the metal shell 150 so that the weld joint 399 can be formed easily assuredly by laser welding.

The entire contents of Japanese Patent Application No. 2007-123106 (filed on May 8, 2007) and No. 2008029567 (filed on Feb. 8, 2008) are herein incorporated by reference.

Although the present invention has been described with reference to the above specific embodiments, the invention is not limited to these exemplary embodiments. Various modification and variation of the embodiments described above will occur to those skilled in the art in light of the above teachings.

For example, the cover engagement portion 57 and the tool engagement portion 52 of the metal shell 50 are not necessarily located adjacent to each other in the first embodiment. A deformable portion may be formed between the cover engagement portion 57 and the tool engagement portion 52 of the metal shell 50 in such a manner that the deformable portion gets deformed to disperse a reaction force caused by formation of the swaged portion 53 and maintain the swaged portion 53 in its proper swaged state. Such a deformable portion may also be formed in the metal shell 150 in the second to fourth embodiments.

Although the front end face 69 of the protection cover 65 is held in contact with the step 574 of the metal shell 50 in the first embodiment, the front end face 69 of the protection cover 65 and the step 574 of the metal shell 50 may alternatively be spaced away from each other.

The swaging process may be performed between the cover placement process and the swaging process so as to swage the front end 166, 266, 366 of the protection cover 165, 265, 365 onto the metal shell 150 for tentative fixing of the protection cover 165, 265, 365 in the second to fourth embodiments as in the case of the first embodiment. Furthermore, the swaging process is not necessarily performed for tentative fixing of the protection cover 65 to the metal shell 50 in the first embodiment. The protection cover 65 may be fitted onto the metal shell 50 by adjusting the inner diameter of the protection cover 65 and the outer diameter of the metal shell 50 (notably, the small-diameter section 572) in such a manner that the front end 66 of the protection cover 65 fits with and does not become readily detached from the cover engagement portion 57 of the metal shell 50.

The scope of the invention is defined with reference to the following claims.

What is claimed is:

1. A method of manufacturing a gas sensor, comprising:
providing a sensor element, a cylindrical metal shell and a cylindrical protection cover, the sensor element having a gas sensing portion at a front end thereof and an electrode portion at a rear end thereof, the metal shell having a flange portion and a rear end portion located on a rear side of the flange portion and including a first cylindrical section and a second cylindrical section located on a rear side of the first cylindrical section and being smaller in diameter than the first cylindrical section;
assembling the sensor element and the metal shell together to retain the sensor element in the metal shell with the gas sensing portion and the electrode portion protruding from front and rear ends of the metal shell, respectively;
placing a front end of the protection cover around the second cylindrical section of the rear end portion of the metal shell and allowing an end face of the front end of the protection cover to abut a rear end face of the first cylindrical section of the rear end portion of the metal shell, wherein the front end of the protection cover is placed around the second cylindrical section of the rear end portion of the metal shell;
swaging the front end of the protection cover and the rear end portion of the metal shell radially inwardly to form a swaged part circumferentially astride from the end face of the front end of the protection cover to the first cylindrical section of the rear end portion of the metal shell; and
laser welding the entire circumference of the front end of the protection cover to the first cylindrical section of the rear end portion of the metal shell to form a weld joint therebetween, in the swaged part, extending from the end face of the front end of the protection cover to the first cylindrical section of the rear end portion of the metal shell.

2. The method according to claim 1, wherein said laser welding is performed in such a manner that a penetration depth of the weld joint is larger than a thickness of the protection cover.

3. The method according to claim 2, wherein said laser welding is performed in such a manner that an outer circumferential area of the weld joint is curved in concave form.

4. A method of manufacturing a gas sensor, comprising:
providing a sensor element, a cylindrical metal shell and a cylindrical protection cover, the sensor element having a gas sensing portion at a front end thereof and an electrode portion at a rear end thereof, the metal shell having a flange portion and a rear end portion located on a rear side of the flange portion;
assembling the sensor element and the metal shell together to retain the sensor element in the metal shell with the gas sensing portion and the electrode portion protruding from front and rear ends of the metal shell, respectively;
placing a front end of the protection cover around the rear end portion of the metal shell and allowing an end face of the front end of the protection cover to abut a rear end face of the flange portion of the metal shell;
swaging the front end of the protection cover and the rear end portion of the metal shell radially inwardly to form a swaged part circumferentially astride from the end face of the front end of the protection cover to the rear end portion of the metal shell; and
laser welding the entire circumference of the front end of the protection cover to the flange portion of the metal shell to form a weld joint therebetween extending from the end face of the front end of the protection cover to the flange portion of the metal shell, wherein the weld joint is formed in the swaged part so as to extend from the end face of the front end of the protection cover to the rear end portion of the metal shell.

5. A method of manufacturing a gas sensor, comprising:

providing a sensor element, a cylindrical metal shell and a cylindrical protection cover, the sensor element having a gas sensing portion at a front end thereof and an electrode portion at a rear end thereof, the metal shell having a flange portion and a rear end portion located on a rear side of the flange portion;

assembling the sensor element and the metal shell together to retain the sensor element in the metal shell with the gas sensing portion and the electrode portion protruding from front and rear ends of the metal shell, respectively;

placing a front end of the protection cover around the rear end portion of the metal shell while spacing an end face of the front end of the protection cover away from the flange portion of the metal shell;

swaging the front end of the protection cover and the rear end portion of the metal shell radially inwardly to form a swaged part circumferentially astride from the end face of the front end of the protection cover to the rear end portion of the metal shell; and laser welding, at the swaged part, the entire circumference of the front end of the protection cover to the rear end portion of the metal shell to form a weld joint therebetween extending from the end face of the front end of the protection cover to the rear end portion of the metal shell, wherein a front end of the weld joint is located at a distance of 1 mm or greater from the rear end of the flange portion of the metal shell.

6. The method according to claim 5, wherein said laser welding is performed in such a manner that an outer circumferential area of the weld joint is curved in concave form.

7. A gas sensor, comprising:

a sensor element extending axially of the gas sensor and having a gas sensing portion at a front end thereof and an electrode portion at a rear end thereof;

a cylindrical metal shell retaining therein the sensor element with the gas sensing portion and the electrode portion protruding from front and rear ends of the metal shell, respectively, and having a flange portion and a rear end portion on a rear side of the flange portion;

a cylindrical protection cover having a front end fitted onto the rear end portion of the metal shell so as to cover the electrode portion; and a weld joint through which the entire circumference of the front end of the protection cover is joined to the metal shell, wherein the weld joint extends from an end face of the front end of the protection cover to the metal shell, wherein a front end of the weld joint is located at a distance of 1 mm or greater from the rear end of the flange portion of the metal shell.

8. A gas sensor, comprising:

a sensor element extending axially of the gas sensor and having a gas sensing portion at a front end thereof and an electrode portion at a rear end thereof;

a cylindrical metal shell retaining therein the sensor element with the gas sensing portion and the electrode portion protruding from front and rear ends of the metal shell, respectively, and having a flange portion and a rear end portion on a rear side of the flange portion;

a cylindrical protection cover having a front end fitted onto the rear end portion of the metal shell so as to cover the electrode portion; and a weld joint through which the entire circumference of the front end of the protection cover is joined to the metal shell, wherein the rear end portion of the metal shell includes a first cylindrical section and a second cylindrical section located on a rear side of the first cylindrical section and being smaller in diameter than the first cylindrical section;

wherein the front end of the protection cover is placed around the second cylindrical section of the rear end portion of the metal shell, wherein the front end of the protection cover and the rear end portion of the metal shell are swaged radially inwardly to form a swaged part circumferentially astride from an end face of the front end of the protection cover to the first cylindrical section of the rear end portion of the metal shell, wherein the weld joint is formed in the swaged part so as to extend from the end face of the front end of the protection cover to the first cylindrical section of the rear end portion of the metal shell.

9. The gas sensor according to claim 1, wherein a front end of the weld joint is located at a distance of 1 mm or greater from a rear end of the flange portion of the metal shell.

10. The gas sensor according to claim 1, wherein a penetration depth of the weld joint is larger than a thickness of the protection cover.

11. The gas sensor according to claim 10, wherein the penetration depth of the weld joint is two or more times larger than the thickness of the protection cover.

12. The gas sensor according to claim 1, wherein the weld joint is formed circumferentially so as to extend from the end face of the front end of the protection cover to the flange portion of the metal shell.

13. The gas sensor according to claim 12, wherein the weld joint extends toward the front and toward an axis of the gas sensor.

14. The gas sensor according to claim 12, wherein a penetration depth of the weld joint is larger than a thickness of the protection cover.

15. The gas sensor according to claim 12, wherein an outer circumferential area of the weld joint is curved in concave form.

* * * * *